United States Patent [19]
Brady et al.

[11] Patent Number: 4,678,580
[45] Date of Patent: Jul. 7, 1987

[54] HYDROLYSIS OF FATS

[75] Inventors: Cathereine D. Brady, Downers Grove; Lincoln D. Metcalfe, Lagrange; Dale R. Slaboszewski, Joliet; Dieter Frank, Naperville, all of Ill.

[73] Assignee: Akzo America Inc., New York, N.Y.

[21] Appl. No.: 899,279

[22] Filed: Oct. 14, 1986

Related U.S. Application Data

[62] Division of Ser. No. 823,114, Jan. 27, 1986, Pat. No. 4,629,742.

[51] Int. Cl.⁴ .................................... B01D 25/04
[52] U.S. Cl. ............................. 210/490; 210/500.42; 521/53; 521/84.1
[58] Field of Search ............... 521/53, 84.1; 210/490, 210/500.42

[56] References Cited

U.S. PATENT DOCUMENTS 4,629,742 12/1986 Brady et al. ................... 521/53

OTHER PUBLICATIONS

"Continuous Hydrolysis of Olive Oil Body Lipase in Microporous Hydrophobic Membrane Bioreactor", by Hoq et al, JAOCS, vol. 62, No. 6, (Jun. 1985).
"Continuous Hydrolysis Tallow with Immobilized Lipase in a Microporous Membrane" Taylor et al, Jun. 12, 1985, OS—693, FT:SRM (5/1/85), Agricultural Research Service, U.S. Dept. of Agriculture, Eastern Center.

Primary Examiner—Morton Foelak
Attorney, Agent, or Firm—Louis A. Morris; Francis W. Young

[57] ABSTRACT

A process for the hydrolysis of liquid fats comprising contacting the fats, in the presence of water at hydrolyzing conditions, with lipase immobilized by adsorption from aqueous solution without pretreatment or pretreatment with a polar solvent on a microporous structure comprising a synthetic hydrophobic thermoplastic polymer selected from the group consisting of aliphatic olefinic polymers, oxidation polymers, ionic polymers and blends thereof. Various embodiments of the invention include the immobilized lipase itself and an embodiment that employs a vertical packed column of particles of the immobilized lipase through which the liquid fat and water feed streams may be passed cocurrent or countercurrent, one that employs a horizontally disposed diaphragm that includes a layer of fibers of the immobilized lipase and an embodiment that employs a stirred reactor wherein a suspension of particles of the immobilized lipase is maintained in the reaction medium. The process of the invention has exhibited surprisingly high activity in the hydrolysis of fats and the immobilized lipase possesses significant longevity.

4 Claims, 11 Drawing Figures

HYDROLYSIS OF FATS

This is a division of application Ser. No. 823,114, filed Jan. 27, 1986, now U.S. Pat. No. 4,629,742.

BACKGROUND OF THE INVENTION

The hydrolysis of fats, also known as fat splitting, has long been accomplished by the use of high pressure steam. Steam splitter reaction conditions are typically about 250° C. and 750 psig. To maintain these conditions a boiler is required to supply the high pressure steam as well as sophisticated pumps capable of pumping feedstock and water into the steam splitting column at high pressure. The costs involved for this type of operation, as required for capital investment as well as process costs such as for energy in the forms of steam, natural gas and electricity, are of course, very high.

There is thus a significant economic incentive to develop new more efficient processes for the hydrolysis of fats, and, as has already been demonstrated in Japan, enzymatic fat splitting is clearly the process of choice. The enzyme that catalyzes the hydrolysis of fats is called lipase, or more formally E.C. 3.1.1.3 glycerolester hydrolase. The overall chemistry of the reaction is shown below for a typical triglyceride:

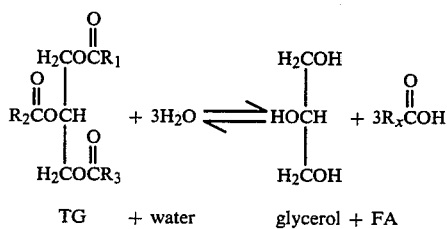

It may be noted that the above reaction actually proceeds via stepwise hydrolysis of the acyl groups on the glyceride, so that any given time, the reaction mixture contains not only triglyceride, water, glycerol, and fatty acid, but also diglycerides and monoglycerides. Furthermore the reaction is reversible. The reverse reaction between an alcohol and a fatty acid to form an ester is called esterification. To force the forward reaction to completion, it is necessary to remove one of the products from the reaction mixture. This task is made easy by the fact that the reaction actually takes place in a biphasic medium. The triglyceride and fatty acid form an oil layer, while the water and glycerol form an aqueous layer. Thus the hydrolysis is easily forced to completion in the splitter by removing the glycerol in the sweetwater.

Lipase can be isolated from several sources soil, plants, animals, or microorganisms. However, there are important differences in the substrate specificity of the lipases harvested from different sources. For example, porcine pancreatic lipase is position specific for the terminal (sn-1 and sn-3) ester bonds on the triglyceride. Lipase from several microbes, such as *Rhizopus arrhizus* and *Mucor miehei* also show the same positional preference for the end acyl groups. Another type of specificity is exhibited by the lipase secreted by *Geotrichum candida*. This lipase preferentially liberates unsaturated fatty acid groups containing a cis double bond in the 9-position of the acyl group, such as oleic and linoleic acids.

A third type of substrate specificity shown by some lipases is that of chain length. Pregastric esterases of lamb, goat, and kid selectively split shorter carbon chain length acyl groups ($C_4$-$C_8$). These lipases, are used in the manufacture of Italian cheeses. The distinctive flavor of these cheeses is caused by the release of short chain fatty acids. Lipase from *Aspergillus niger* has also shown a similar specificity for shorter chain lengths.

Lipases that show no substrate specificity and are thus random in their attack on the glyceride molecule also exist. This is the type of enzyme catalyst that is needed for the fat splitting reaction. The most prevalent nonspecific lipase is isolated from the yeast *Candida cylindracea*, which has been reclassified recently to *Candida rugosa*. Pseudomonas type bacteria have also been found to excrete a nonspecific lipase.

There are many references concerned with enzymatic fat hydrolysis. In *Household & Personal Products Industry*, August 1981, Page 31, there was disclosed the use of lipase in an enzymatic process in which oil and fat are separated into fatty acid and glycerine. Likewise, the following references discuss various methods of effecting enzymatic fat hydrolysis:

A. Mitsutani, *Research & Development Review Report No. 27, Application of Microbiological Technology to Chemical Process*, Nippon Chemtec Consulting, Inc., March 1984.

W. Linfield, R. Barauskas, L. Sivieri, S. Serota, R. Stevenson, "Enzymatic Fat Hydrolysis and Synthesis", *JAOCS*, 61 (2), February 1984, pp. 191-195.

W. Linfield, D. O'Brien, S. Serota, R. Barauskas, "Lipid-lipase Interactions I. Fat Splitting with Lipase from *Candida rugosa*", *JAOCS*, 61 (6), June 1984, pp. 1067-1071.

G. Benzonana, S. Esposito, "On the Positional and Chain Specificities of *Candida Cylindracea Lipase*", *Biochim. Biophys. Acta*, 231 (1971) pp. 15-22.

None of the above references discusses the use of immobilized enzymes. The immobilization of enzymes on solid supports has advantages that have long been recognized. A particular advantage is that the immobilized enzyme remains bonded to the support rather than passing through with the substrate upon which it is acting so that there is no need to recover the enzyme from the substrate and so that the enzyme remains in the support where it may be reused.

Japanese Patent Publication No. JP 84091883 (Abstract No. 84-168208) of May 5, 1984 discloses that an immobilized enzyme may be produced by bringing an aqueous solution of enzyme into contact with a porous synthetic hydrophobic adsorbent. Examples given to adsorbent materials are styrene and methacrylic acid ester. The reference, however, gives no hint to the hydrolysis of fats, nor to lipase as the enzyme.

Russian Patent Publication No. SU 804647 (Abstract No. 83249D) of Feb. 15, 1981 discloses crosslinked porous styrene polymers used as activity enhancing carriers for immobilized enzymes, but also does not hint to the composition, process, methods or apparatus of the present invention.

There is also art that teaches the hydrolysis of fats by use of immobilized lipase. In *Chemical Week*, Vol. 133, No. 22, Nov. 30, 1983, on page 33, it is generally mentioned that a number of useful enzymes may be immobilized by locking them to a carrier by adsorption, crosslinking or covalent bonding, and on page 34 there is mention that lipase may be used to hydrolyze fat, but there is no teaching in this reference of polymeric carriers, and there is a warning on page 33 that an enzyme free in solution and the same enzyme locked to a carrier do not behave the same.

In J. Lavayre, J. Baratti, "Preparation and Properties of Immobilized Lipases", *Biotech & Bioengr.*, 24 (1982), pp. 1007-1013, hereinafter referred to as "Lavayre et al", there is discussed the use of lipase immobilized by adsorption onto a hydrophobic support for the hydrolysis of olive oil. The Lavayre et al article, however, states that when purified pancreatic lipase was used, the specific activity of the immobilized enzyme was 17 to 25% that of the soluble enzyme. Furthermore, the only support used in the hydrolysis tests was the iodopropyl derivative of porous glass (Spherosil).

The use of lipase immobilized onto polyacrylamide beads for the hydrolysis of triglyceride is discussed in "Bell, Todd, Blain, Paterson and Shaw", Hydrolysis of Triglyceride by Solid Phase Lipolytic Enzymes of Rhizopus arrhizus in Continuous Reactor Systems", *Biotech & Bioengr.*, 23 (1981), pp. 1703-1719, and in Lieberman and Ollis, "Hydrolysis of Particulate Tributyrin in a Fluidized Lipase Reactor", *Biotech & Bioengr.*, 17 (1975), pp. 1401-1419. In those references, however, the immobilization is effected by covalent bonding (e.g. diazonium intermediate), not adsorption. The results were a significant decrease in the activity of the immobilized as compared to the free enzyme.

The hydrolysis of fats with lipase is a reversible reaction and there are teachings in the art of methods of producing fats by reacting a fatty acid with water and glycerol in the presence of lipase. One such reference is M. M. Hoq, T. Yamane, S. Shimizu, T. Funada, S. Ishida, "Continuous Synthesis of Glycerides by Lipase in Microporous Membrane Bioreactor", *JAOCS*, 61 (4), April 1984, pp 776-781, hereinafter referred to as "Hoq et al". Hoq et al advises against the use of immobilized lipase for the stated reason that its activity is commonly only several percent of the original activity of the free lipase. Hoq employs a device, it refers to as a bioreactor, which comprises supported hydrophobic microporous membrane, in particular one made from polypropylene, that is placed at the interface of an upper phase of fatty acid and lower phase of a solution of glycerol, water and lipase. The reactants and lipase come into contact at the interface of the two phases thereby causing the reaction, the glycerides diffusing back into the bulk flow of the fatty acid phase.

The present invention is based on the surprising discovery that lipase immobilized on certain porous polymeric supports in a certain manner loses very little of its fat hydrolysis activity as compared to soluble lipase, notwithstanding teachings of prior art such as Lavayre et al and Hoq et al that immobilization of lipase causes such activity to diminish to a small fraction of the free lipase.

SUMMARY OF THE INVENTION

It is a primary objective of the present invention to obtain a composition comprising an immobilized lipase that has a unique suitability for use in a process for the hydrolysis of fats. Another objective is to obtain a process for the hydrolysis of fats using such immobilized lipase without significant sacrifice of lipase activity as compared to free soluble lipase. Other objectives are to provide a method for the immobilization of the lipase as well as means and devices which use the immobilized lipase of the invention in a practical and efficient manner.

Accordingly, the present invention, in a first embodiment is a composition comprising lipase immobilized by adsorption from aqueous solution on a microporous structure comprising a synthetic hydrophobic thermoplastic polymer selected from the group consisting of aliphatic olefinic polymers, oxidation polymers, ionic polymers and blends thereof. The structure is not pretreated prior to the adsorption or is pretreated by wetting with a polar water miscible organic solvent in which the polymer is insoluble and which does not deactivate the lipase.

In a second embodiment, the present invention comprises a method for the immobilization of lipase on a microporous structure comprising a synthetic hydrophobic thermoplastic polymer selected from the group consisting of aliphatic olefinic polymers, oxidation polymers, ionic polymers and blends thereof. The immobilization is effected either without pretreatment of the structure or is pretreated by first wetting the polymer with a polar water miscible organic solvent in which such polymer is insoluble and which does not deactivate the lipase. The support is then soaked in a dilute aqueous solution of the lipase.

In a third embodiment, the present invention comprises a process for the hydrolysis of liquid fats. The process comprises contacting liquid fats, in the presence of water at hydrolyzing conditions, with lipase, immobilized by adsorption from aqueous solution on a microporous structure. The structure comprises a synthetic hydrophobic thermoplastic polymer selected from the group consisting of aliphatic olefinic polymers, oxidation polymers, ionic polymers and blends thereof. The structure may be pretreated prior to adsorption only by wetting with a polar water miscible organic solvent in which the polymer is insoluble and which does not deactivate the lipase. Pretreatment, however, is not essential.

In a fourth embodiment, the present invention comprises a process for the hydrolysis of liquid fats comprising contacting the fats in the presence of water at hydrolyzing conditions with lipase immobilized by adsorption from aqueous solution on a microporous structure comprising a synthetic hydrophobic thermoplastic polymer selected from the group consisting of aliphatic olefinic polymers, oxidation polymers, ionic polymers and blends thereof. The structure is either not pretreated or is pretreated prior to adsorption only by wetting with a polar water miscible organic solvent in which the polymer is insoluble and which does not deactivate the lipase. The contacting is effected by means of a column packed with a powder of the structure on which the lipase is immobilized. The powder in the cocurrent embodiment is preferably from about 150 to about 450 micron particle size.

In a fifth embodiment, the present invention is a process for the hydrolysis of fats. The process comprises maintaining a lower liquid phase of fats and an upper liquid phase which comprises water. The phases are separated at their interface with a horizontally disposed diaphragm which comprises three layers. The bottom most layer is a hydrophobic filter cloth. The middle layer is fibers of a support comprising a synthetic microporous thermoplastic polymer having lipase immobilized thereon. The top most layer of the diaphragm is a retaining means capable of maintaining the fibers of the middle layer in place. The fats flow upward through the bottom layer and into contact with the supported lipase of the middle layer, where in the presence of water from the upper phase, and, at hydrolyzing conditions, the hydrolysis of the fats occurs. The fatty acids product of the hydrolysis rises to the surface of the upper phase to form a separate uppermost phase. The glycerol product of the hydrolysis dissolves in the upper phase and the fatty acids are removed as the uppermost phase and glycerol products are recovered from the upper phase. Additional fats and water are added as required to maintain the desired inventory of each.

In a sixth embodiment, the present invention is a process for the hydrolysis of fats which comprises maintaining a suspension comprising lipase immobilized by adsorption from aqueous solution on particles of a microporous structure. The process employs a synthetic hydrophobic thermoplastic polymer which is selected from the group consisting of aliphatic olefinic polymers, oxidation polymers, ionic polymers and blends thereof, in a liquid reaction mixture. The structure may be pretreated prior to the adsorption by wetting with a polar water miscible organic solvent in which the polymer is insoluble and which does not deactivate the lipase. Pretreatment, however, is not essential. The reaction mixture comprises fats and water and is maintained by the continuous addition thereto of a stream of liquid fats and water. A portion of the reaction mixture containing reaction products which comprise fatty acids and a glycerol solution is continuously withdrawn.

A seventh embodiment of the present invention is an apparatus related to the above fifth embodiment comprising a diaphragm suitable for use in the hydrolysis of fats comprising:

a. a first layer consisting of a hydrophobic filter cloth having openings from about 3 to about 5 microns in size;

b. a second layer adjacent to said first layer comprising fibers of a hydrophobic microporous thermoplastic polymer selected from the group consisting of aliphatic olefinic polymers, oxidation polymers, ionic polymers and blends thereof, having lipase immobilized on the fibers by adsorption from an aqueous solution either without pretreatment or following pretreatment of the fibers only by wetting with a polar water miscible organic solvent in which the polymer is insoluble and which does not deactivate the lipase; and c. a third layer adjacent to the side of said second layer opposite said first layer comprising a retaining means capable of maintaining the fibers of the second layer in place.

Other embodiments of the present invention encompass details about process flow schemes, reaction conditions and materials compositions, and mechanical details all of which are hereinafter disclosed in the following discussion of each of the facets of the present invention.

DESCRIPTION OF THE INVENTION

Figure 1:
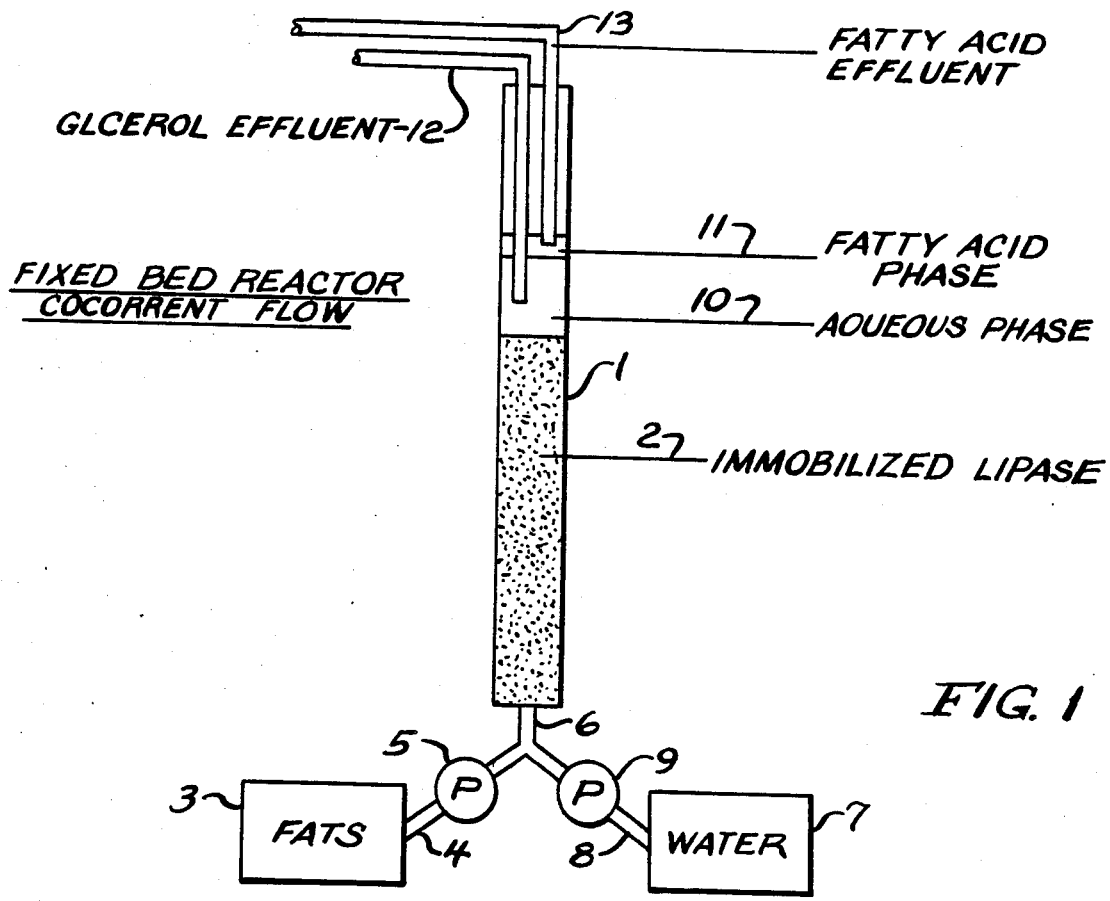
FIGS. 1 and 2 are, respectively, elevation views of the embodiment of the invention comprising cocurrent and countercurrent flow packed columns.

There has long been an interest and unfulfilled need to immobilize lipase for use in fat splitting, particularly Candida lipases in view of their high activity for that purpose. A primary reason for such need is the high cost of such lipase which dictates that it be used in an immobilized form so that it can be reused many times. Otherwise, the enzymatic fat splitting process, at least in view of current costs of enzymes and energy, could never be competitive with non-catalytic high pressure steam fat splitting.

As mentioned above, however, the prior art teaches that the immobilization of lipase causes its activity to diminish to a small fraction of free lipase. The present inventors, therefore, were greatly surprised to find that little if any of such activity was lost when the lipase was immobilized on an appropriate porous polymeric support.

At about the time of the discovery of the surprising utility of lipase immobilized on porous polymeric support for fat splitting was the discovery that when immobilization was carried out in a certain way, an even superior product was obtained. The method then thought to be best for immobilization involved pretreating the polymer with a metal salt solution (e.g. stannous chloride) and/or a long chain cationic solution (e.g. a salt of N-coco-1,3-diaminopropane or trimethyltallowammonium chloride). The enzyme was then immobilized onto the pretreated polymer. When immobilization experiments started with lipase and polymeric supports for the splitting of fats, however, it was noted that not only did the pretreatment have no positive effect on the activity of the immobilized lipase, a lack of pretreatment (other than wetting the support with a polar solvent) was found to be beneficial.

The method of immobilization found to be most effective is to simply soak the support in a dilute aqueous solution of the lipase, or, optionally, first wet the polymer structure with a polar water miscible organic solvent in which the polymer is insoluble and which does not deactivate the lipase. The concentration of the lipase solution may vary. A dilute solution is about 35 lipase units per ml., while concentrated would be about 500 units per ml. A unit is defined as the amount of lipase required to produce one micro-mole of fatty acid per minute from an olive oil substrate under the conditions of the assay, typically at a pH of 7° and 35° C. The pH of the lipase solution is not important, and may be buffered to any value, with an optimum between about 4 to about 7.

The term "polar" as used herein shall mean the property of having a dipole moment of at least 0.1 debye. The term "water miscible" shall mean capable of mixing in any ratio with water without separation of phases. The term "insoluble" shall mean a solubility in the solvent in question of not greater than 0.1 g/l. The term "deactivate" shall mean the loss of the ability to catalyze the hydrolysis reaction.

The hydrophobic microporous cellular polymer selected must be a microporous (about 0.1-500 micron average pore diameter) synthetic hydrophobic thermoplastic polymer selected from the group consisting of aliphatic olefinic polymers, oxidation polymers, ionic polymers and blends thereof. Polypropylene and polyethylene are examples of nonionic polymers. The binding of lipase to the nonionic polymers is by hydrophobic adsorption. A minimum hydrophobicity is essential for the nonionic polymers. Nonionic polymers effective for the present invention, and having a sufficient degree of hydrophobicity, are considered to be those having a surface tension less than 41 dynes/cm which includes polyethylene and polypropylene. For the ionic polymers, e.g. Surlyn ®, the binding of lipase to polymer may no longer be simply hydrophobic bonding, but rather complicated by ionic interactions. Thus, surface tension would no longer be a relevant parameter. For these polymers for which surface tension is not a relevant parameter, the term "hydrophobic" may have its commonly understood meaning as defined in *Hackh's Chemical Dictionary*, 4th Edition, i.e. a substance that does not adsorb or absorb water.

The ideal microporous structure for the polymeric supports and method of obtaining such structure are as disclosed in U.S. Pat. Nos. 4,247,498 and 4,519,909 issued to Castro, both incorporated by reference herein in their entirety. Those patents disclose micorporous cellular polymer structures known by the trademark Accurel ® which are marketed by Enka America Incorporated, 1827 Walden Office Sq., Suite 480, Schaumburg, Ill. 60195. Accurel ® structures may be characterized in one of three ways:

1. a cellular microporous structure which comprises a plurality of substantially spherical cells having an average pore diameter from about 0.5 to about 100 microns, distributed substantially uniformly throughout the structure, adjacent cells being interconnected by pores smaller in diameter than the microcells, the ratio of the average cell diameter to the average pore diameter being from about 2:1 to about 200:1, the pores and the cells being void.
2. A cellular microporous structure which is cellular and is characterized by a C/P ratio of from about 2 to about 200, an S value of from about 1 to about 30, and an average cell size from about 0.5 to about 100 microns.
3. An isotropic microporous structure that is characterized by an average pore diameter of from about 0.1 to about 5 microns and an S value of from about 1 to about 10.

In numbers 2 and 3 above "C" means average diameter of cells, "P" the average diameter of the pores, and "S" is the sharpness factor, determined by use of a Micromeritics Mercury Penetration Porosimeter, and defined as the ratio of the pressure at which 85 percent of the mercury penetrates the structure to the pressure at which 15 percent of the mercury penetrates.

MEANS TO ACHIEVE THE CONTACTING OF THE REACTANTS WITH THE IMMOBILIZED LIPASE

One means to achieve the contacting of the liquid fats with the immobilized lipase is a column packed with discrete particles of the immobilized lipase. The fixed bed column reactor is a very common design for immobilized enzyme reactors. In this type of reactor fats and water may either be passed concurrently through the column in a direction parallel to the longitudinal axis of the column, or countercurrently through the column in directions parallel to the longitudinal axis of the column. In a packed column, the activity of the lipase may be restored by first flushing the contents of the column with a solvent suitable for the removal of spent lipase and residual fat from the porous polymeric support (e.g. alcohol), then flushing the contents of the column with water to remove the solvent, then flushing with a broth of fresh lipase and finally flushing the contents of the column with water to wash away excess enzyme.

With the cocurrent type flow scheme fats and water are passed into the column at one end and reaction products comprising glycerol and fatty acids are removed at the opposite end. FIG. 1 illustrates the cocurrent fixed bed immobilized lipase reactor including vertical column 1 packed with bed 2 of particles of immobilized lipase. The particles are preferably in the form of powder of from about 150 to about 450 microns in particle size. Liquid fats are passed from tank 3 via conduit 4 and pump 5 into mixing conduit 6, and water is passed from tank 7 via conduit 8 and pump 9 into mixing conduit 6. In mixing conduit 6 vigorous mixing is effected so as to obtain a fat/water emulsion which passes into column 1 and one end of bed 2. The reaction mixture is passed through bed 2 over a period of time from about 2 to about 10 hours (or longer, depending on the degree of conversion desired). The reaction mixture exits the top of bed 2 and separates into an aqueous phase 10, also referred to as "sweetwater" since that is where dissolved glycerol product accumulates, and fatty acid phase 11. Aqueous phase product may periodically or continuously be drawn off via conduit 12 and fatty acid phase product may be drawn off via conduit 13.

Figure 2:
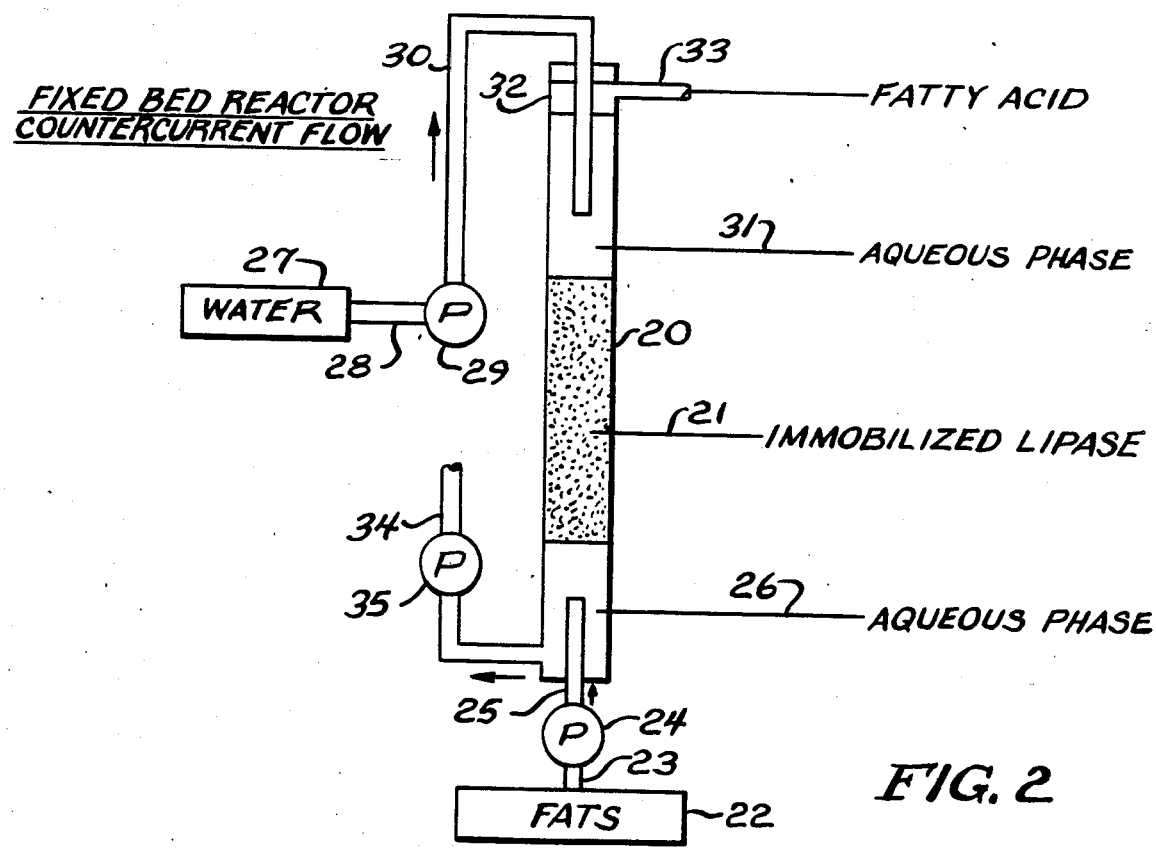

FIG. 2 illustrates the countercurrent fixed bed immobilized lipase reactor, including vertical column 20 packed with bed 21 of particles of immobilized lipase. Liquid fats are passed from tank 22 via conduit 23, pump 24 and conduit 25 into the bottom of column 20 and first aqueous phase 26. Water is passed from tank 27 via conduit 28, pump 29 and conduit 30 into the top of column 20 and second aqueous phase 31. The water and fats will flow countercurrently through bed 21 due to the effect of gravity and the difference in specific gravity between the phases, the fats being the lighter of the two phases. The temperature and residence time of the reactants in bed 21 will be about the same as for the above cocurrent reactor. Fatty acid will accumulate in fatty acid phase 32 and may periodically or continuously be drawn off via conduit 33, while at the same time sweetwater is drawn from aqueous phase 26 via conduit 34 and pump 35.

Figure 3:
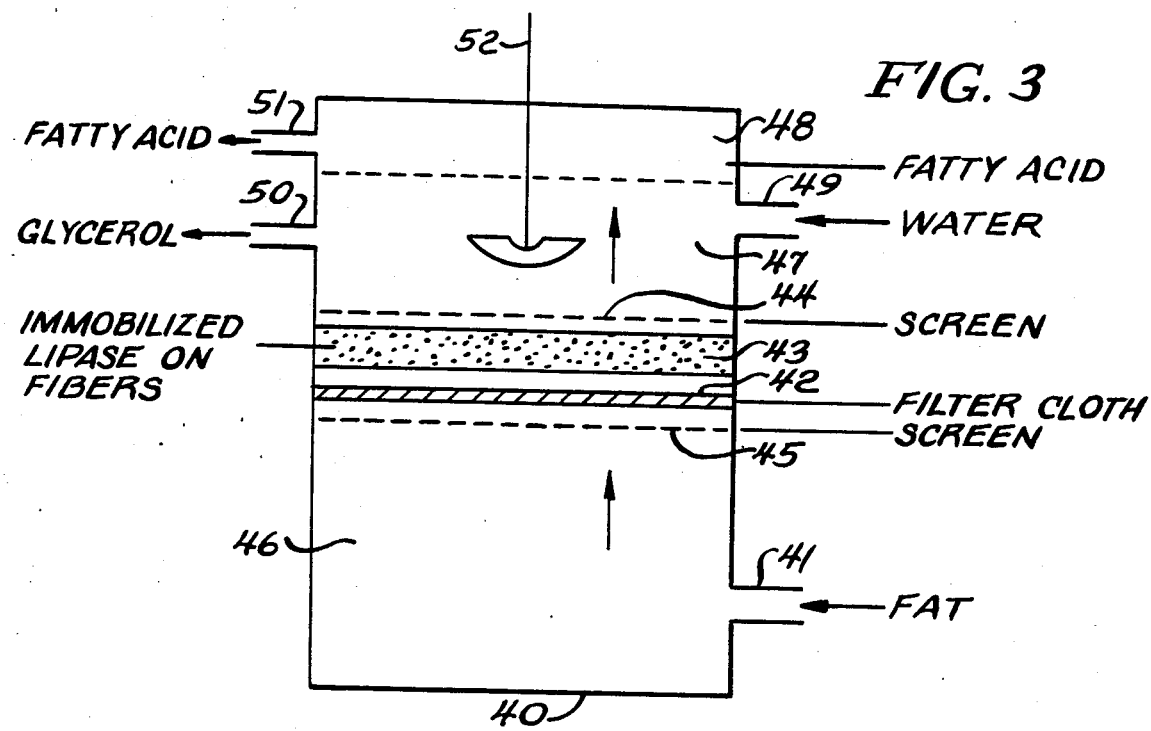
FIG. 3 is illustrative of the embodiment of the invention employing a multi-layered diaphragm.

Another type of continuous fat hydrolysis reactor is the diaphragm reactor as illustrated in FIG. 3. Fat in a liquid form enters a bottom portion of vessel 40 via conduit 41. Vessel 40 is separated into a bottom and top portion by a horizontal diaphragm comprising three layers. The bottom most layer 42 is a hydrophobic filter cloth. Suitable materials for filter cloth 42 are PTFE (Teflon) and polypropylene. The middle layer 43 comprises fibers of the porous polymeric support on which the lipase is immobilized. The fibers that have heretofore been used averaged about 3–7 microns in diameter. The thickness of the fiber layer heretofore observed, following compression through use was about 2–4 mm. The top most layer 44 is a retaining means capable of keeping the fibers in place and may comprise any type of screen having appropriately sized openings. There may be an additional screen 45 supporting the entire diaphragm if filter cloth 42 is considered inadequate for that purpose.

Choice of the hydrophobic filter cloth comprising bottom most layer 42 is particularly important. The openings in the cloth must be large enough to permit an acceptable flow rate of fat through the cloth, but not so large that water would pour through from above. Filter cloths found to be effective were Gore-Tex ® Expanded PTFE Membranes and Laminates with 3–5μ openings from W. L. Gore and Associates, Inc. and 0.5–1.0 CFM rated (air flow measured at ½" H₂O pressure on a Frazier Permeometer) PP cloth from CrosIble, Inc.

In operation, the diaphragm will serve to separate at their interface a lower liquid fat phase 46 and an upper water phase 47. The fats will flow upward through bottom layer 42 and come into contact with the supported lipase of middle layer 43 where in the presence of the water from the upper phase 47, and with a residence time in the diaphragm itself of from about 20 minutes to about 60 minutes, the hydrolysis of the fats will occur. The fatty acids that are formed, rather than remaining in the fat phase, will advantageously due to their inherent buoyancy, rise to the surface of the upper phase 47 to form a separate uppermost phase 48. The glycerol product of the hydrolysis will dissolve in the upper aqueous phase 47.

Water may enter the top portion of tank 40 via conduit 49. Fatty acid may be withdrawn as a product stream via conduit 51 and glycerol via conduit 50. Stirrer 52 will serve to maintain a reasonably homogeneous solution in phase 47. Additional fat and water may be added as required to maintain the desired inventory of each.

In the process as shown in FIG. 3, the activity of the lipase with respect to the hydrolysis of the fats may be restored by flushing the diaphragm sequentially with three flushing liquids which enter the diaphragm at top layer 44 and exit through a means provided to bypass the filter cloth, such as a conduit and valve. The first flushing liquid comprises a solution of water and a solvent suitable for the removal of spent lipase from the support. Suitable solvents are the same as those that may be used to pretreat the polymer in effecting the initial immobilization. The second flushing liquid comprises a broth of fresh lipase. The third flushing liquid comprises water.

Figure 4:
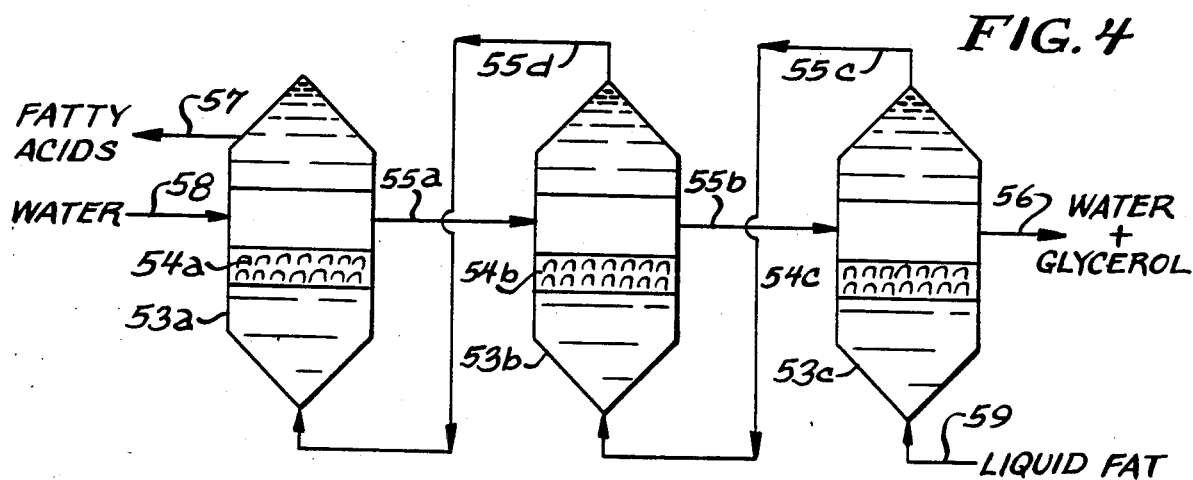
FIG. 4 is illustrative of a multi-diaphragm embodiment of the invention.

A multi-stage diaphragm reactor is as illustrated in FIG. 4. Each stage in this illustration comprises a separate vessel in which a diaphragm is contained. Three vessels, 53a, 53b and 53c, are shown, but any number (two or more) may be used. Diaphragms 53a, 53b and 53c, as described above, of horizontal orientation are placed in sealed contact with the interior surface of the walls of vessels 54a, 54b and 54c, respectively. Conduits 55a and 55b connect vessels 53a to 53b and vessels 53b to 53c, respectively, at points immediately above the diaphragms in each vessel. Conduits 55c and 55d connect vessels 53c to 53b and vessels 53b to 53a, respectively, at points above the diaphragms of vessels 53c and 53b and at or near the tons of those vessels to below the diaphragms of vessels 53b and 53a. There is a water-glycerol product withdrawal conduit 56 connected to vessel 53c immediately above diaphragm 54c. There is a fatty acid product withdrawal conduit 57 connected to vessel 53a above diaphragm 54a and at or near the top of the vessel. There is a water inlet conduit 58 connected to vessel 53a above diaphragm 54a. There is a liquid fat (oil) inlet conduit 59 connected to vessel 53c below diaphragm 54c.

The apparatus of FIG. 4 may be used for that embodiment of the process of the present invention, employing a multiplicity of the diaphragms discussed above with reference to FIG. 3. Since the conversion per pass of the diaphragm appears to not be extremely high, multiple stages are considered advantageous. In using the multi-diaphragm scheme of the invention, as shown in FIG. 4, each diaphragm is associated with a stage which also includes the lower, upper and uppermost phases as discussed above. Each stage is contained in a separate vessel. For reason of simplicity, various pumps and control valves that one skilled in the art would understand to be required are not shown in FIG. 4.

In the operation of the apparatus of FIG. 4, the direction of flow of the non-aqueous streams from vessels 53c to 53b to 53a via lines 55c and 55d is considered "downstream" flow. Conversely, the direction of flow of the aqueous streams from vessels 53a to 53b to 53c via lines 55a and 55b is considered "upstream" flow and countercurrent to the non-aqueous stream. The liquid fat to the process is introduced to vessel 53c via line 59 below diaphragm 54c into the lower phase of the first upstream stage. The water to the process is introduced to vessel 53a via line 58 into the upper phase of the last downstream stage above diaphragm 54a. Although line 58 is shown as passing the water directly into the upper phase in vessel 53a, it may be more convenient to introduce the water at the top of the vessel into the uppermost phase whereupon it would simply flow through the uppermost non-aqueous phase, with which it is immiscible, and thereby, in effect, be introduced into the upper phase. The aqueous stream from the upper phase of each stage in vessels 53a and 53b is passed via lines 55a and 55b, respectively, to the upper phases of vessels 53b and 53c, respectively, while the aqueous stream from the upper phase of the first upstream stage in vessel 53c is withdrawn as the glycerol product steam via line 56. The non-aqueous stream from the uppermost phases of the stages in vessels 53c and 53b are passed via lines 55c and 55d, respectively, to the lower phases of the stages in vessels 53b and 53a, respectively, while the non-aqueous stream from the uppermost phase of the stage in vessel 53a is withdrawn as the fatty acid product stream via line 57.

The embodiment of the present invention illustrated in FIG. 4 is only one possible way of achieving a multi-stage configuration. There are other possibilities including a multiplicity of diaphragms in a single vessel. The FIG. 4 configuration, however, is considered advantageous from the standpoint of simplicity of construction of the equipment and its operation.

Figure 5:
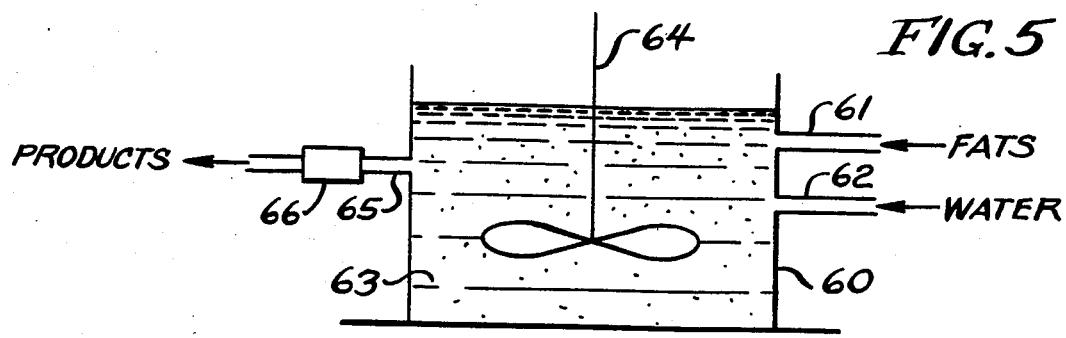
FIG. 5 is illustrative of the stirred reaction embodiment of the invention.

Yet another type of continuous fat hydrolysis reactor is one as illustrated in FIG. 5 which employs a suspension in the liquid reaction mixture of particles of immobilized lipase. This embodiment of the invention may be referred to as the "stirred reactor" or "CSTR".

Looking to FIG. 5, fats and water streams are continuously introduced into vessel 60 via lines 61 and 62, respectively. Particles or a powder of the polymer support on which the lipase is adsorbed are kept in suspension in reaction medium 63 by means of stirrer 64. A portion of the reaction mixture containing the fatty acids and glycerol solution products is continuously withdrawn via line 65. The residence time in reaction medium 63 may comprise from about 2 to about 60 hours.

There is preferably a filter 66 associated with line 65 to enable recovery of the products along with the retention of the particles in the reaction mixture.

As far as reaction conditions for the fat splitting process of the present invention are concerned, the most important consideration is that the temperature be high enough to enable the fat to be in liquid phase but not so high as to cause deactivation of the lipase. Deactivation of *Candida cylindracea* becomes significant at about 50° C. The pH of the reaction mixture is not critical, but it may be maintained at about 7.0 by use of water reactant buffered with sodium phosphate.

EXAMPLES

The following non-limiting examples will serve to illustrate the preferred and advantageous method for achieving immobilization of lipase on a porous polymeric support, the superiority of lipase immobilized on such support in a process for the hydrolysis of fats, and various embodiments of the present invention employing certain devices and flow schemes.

EXAMPLE 1

In this example is it shown that pretreatment of Accurel® prior to lipase immobilization thereon with anything other than a polar solvent is disadvantageous. Four samples were prepared of *Candida cylindracea* lipase immobilized on polypropylene Accurel® powder. The *Candida cylindracea* lipase for this example was obtained from Sigma Chemical Co. as its Type VII Lipase, catalog no. L-1754, with a stated activity of 470 U/mg solid. On three of the four samples Accurel® was pretreated with various materials. On one sample the immobilization was effected by first wetting the polymer with ethanol and then, without further pretreatment, soaking the support in a dilute aqueous solution of the lipase. The results obtained are as shown in Table 1.

TABLE 1

| Pretreatment | Lipase Activity* (IU/g) |
|---|---|
| 1. Ethanol | 103 |
| 2. SnCl$_2$ + ethanol | 91 |
| 3. N—coco-1,3-diaminopropane + ethanol | 83 |
| 4. SnCl$_2$ + N—coco-1,3-diaminopropane + ethanol | 76 |

*Lipase activity units (IU's) are a measure of the micro moles of fatty acid per minute titrated from an olive oil substrate at a pH of 8 and room temperature.

The results from Table 1 illustrate that not only is pretreatment (other than only with a polar solvent) unnecessary, significantly improved activity is realized when pretreatment, other than with a polar solvent, is avoided.

EXAMPLE 2

In this example there was an investigation of the use of various solvents to prewet Accurel® polypropylene powder (150–450u) before the immobilization on such powders of lipase (*Candida cylindracea*) from solution. The lipase obtained for this example was from Enzyme Development Corporation, and is known as Enzeco® lipase with a stated activity of 30,000 U/g. Also investigated was the same powder that was not prewetted prior to immobilization. The procedure in each case to obtain the immobilized lipase was as follows:

1. 1 g of powder was prewet with solvent (except where prewetting was not to occur);
2. 0.2 g. of the lipase was dissolved in 100 ml. of water buffered to pH 7.0 with 0.1M sodium phosphate;
3. the powder was soaked in the lipase solution for thirty minutes; and
4. the resulting immobilized lipase was filtered from the solution and flushed three times with additional quantities of water buffered as above.

A series of tests was then run wherein each of the immobilized lipase samples prepared by the above procedure was used to hydrolyze fat. In each test 50 ml. of Bleachable Fancy Tallow was stirred in a beaker with the immobilized lipase and 100 ml. of buffered water at 42° C. over a 24 hr. period. The results obtained, in terms of % fatty acids in the non-aqueous product phase, at the end of the 24 hour period, are as given in the following Table 2:

TABLE 2

| Pretreatment | % FA |
|---|---|
| ethanol | 58.0 |
| isopropanol | 58.2 |
| methanol | 55.9 |
| acetone | 51.0 |
| tetrahydrofuran | 52.6 |
| none | 66.0 |

The above results show that high levels of fatty acid may be obtained either when pretreatment is effected with a polar solvent, or where there has been no pretreatment. In the latter case the highest degree of fat hydrolysis is achieved, but as will be discussed in the following example, prewetting with a polar solvent greatly facilitates the rate at which the lipase may be immobilized.

EXAMPLE 3

To illustrate a further advantage of the method of lipase immobilization of the present invention, a determination was made of the time required to obtain the immobilization of lipase on a polypropylene Accurel® in a powdered form (150–450 u) and pretreated with ethanol. Immobilization could be effected in about two minutes. Without any pretreatment immobilization took about five times as long. Thus, although pretreatment with the appropriate polar solvent is not necessary to obtain high activity immobilized lipase, it will enable rapid loading of the lipase onto the support which is particularly advantageous with in situ loading and regeneration.

EXAMPLE 4

For this example *Candida cylindracea* lipase (the same as the aforementioned Enzeco® lipase) was immobilized on untreated Accurel® products (treated only with a polar organic solvent) by simple adsorption from a buffered enzyme solution. The procedure for a typical immobilization was to dissolve 0.20 grams of lipase in 100 milliliters of 0.1M sodium phosphate, pH 7.0 buffer. Next, 1.0 gram of Accurel® powder was prewet with as little 3A ethanol as possible and added to the enzyme solution. After stirring for 5–60 minutes, the immobilized catalyst was filtered and then rinsed with several bed volumes of buffer. The immobilized lipase was assayed for activity using a triglyceride substrate, such as olive oil or Bleachable Fancy Tallow.

Other materials, besides Accurel® were screened as supports for lipase. Table 3 lists all the enzyme support materials that were screened and lists the fatty acid levels generated during the assay at 6 and 24 hours on a tallow substrate relative to the soluble lipase as a control. The surprising result was that the porous polymer powders of the present invention performed as vastly superior supports for lipase. Specifically, polypropylene (PP), high density polyethylene (HDPE), and Surlyn® Accurel® powders, the more hydrophobic of the polymers used, were superior supports.

On the other hand, inferior results were obtained from polymers of low hydrophobicity such as cellulose and nylon (nylon is also a condensation polymer which is not a genus of polymer included in the invention), olefinic polymers which are not aliphatic (styrene) and non-polymeric material as well as non-porous material.

Furthermore, comparison of the immobilized enzyme results with those of the soluble lipase control in Table 3 indicates that very little of the lipase activity was lost upon immobilization on these supports. This result is diametrically opposite claims in the literature, as previously discussed, that lipase loses 75–99% of its activity upon immobilization.

TABLE 3

Lipase Immobilization Supports

| Support | % FA by GPC* Relative to Soluble Lipase | |
|---|---|---|
| | 6 HR | 24 HR |
| Johns-Manville | | |
| Celite 545 | 8% | 12% |
| Celkate | 12 | |
| R-600 | 15 | |
| R-640 | 15 | 19 |
| CS-30K | 15 | 17 |
| Misc | | |
| Microcrystalline Cellulose: | | |
| Avicel | 16 | 21 |
| Avicel, 28μ | 19 | 23 |
| Avicel, 50μ | 16 | 29 |
| Ethyl Cellulose | 31 | 52 |
| Silica Gel | 22 | 23 |
| Kieselguhr | 19 | 30 |
| Bentone Clay | 12 | 13 |
| Alumina, neutral | 8 | 9 |
| CPG-100 | 42 | |
| Glycophase-G | 15 | |
| Styrene dvb × 4% (non-porous) | 11 | |
| Celgard 2500 (Celanese Corporation) | 75 | 85 |
| Amberlite XAD-2 (porous styrene) | 8 | 9 |
| Hercules Profax-PP (non-porous) | 15 | 14 |
| USI Microthene-HDPE (non-porous) | 13 | 12 |
| Tenax (porous oxidation polymer of 2,6 di-phenylparaphenylene oxide) | 75 | 82 |
| Versapor 200 (porous acrylic copolymer cast on nonwoven nylon) | 9 | 9 |
| AP-200 (porous acrylic copolymer cast on nonwoven polyester) | 9 | 11 |
| Accurel Powders | | |
| Nylon | 16 | 18 |
| Surlyn | 82 | 88 |
| HDPE 150μ | 93 | 98 |
| HDPE 150–450μ | 62 | 76 |
| PP - std. grind | 73 | 88 |
| PP - Enka | 78 | 88 |
| PP - Friable | 86 | 99 |
| PP - Friable | 73 | 91 |
| PP - Friable | 72 | 88 |
| PP - Friable | 81 | 88 |
| Control | | |
| Soluble Lipase | 100 | 100 |

*1.0 gm support, 3750 IU's Lipase, 1 hour immobilization; 50 mls BFT, 100 mls buffer, 40° C.

EXAMPLE 5

This example describes the operation of fixed bed column reactors as illustrated in FIGS. 1 and 2.

The fixed bed column reactor is a very common design for immobilized enzyme reactors. The columns studied for splitting fat contained lipase immobilized on some form of Accurel ®. Accurel ® products used as support materials in the columns were Enka America Incorporated melt blown PP Accurel ® fibers, Enka's HDPE Accurel ® granules (2–3 mm), and HDPE Accurel ® powder (150–450 microns). The lipase was immobilized on the Accurel ® by simple adsorption. In all cases, lipase from Candida (Enzeco ®, as specified above) was dissolved in 0.1M, pH 7.0, sodium phosphate buffer, the support was prewet with 3A ethanol, and then the support was contacted with the lipase solution. These steps were performed either in a batchwise process in a beaker or in the column reactor itself.

To get an idea of how much of the lipase actually adsorbed on the support, samples of the lipase solution before and after contact with the support and/or samples of the support material before and after contact with the lipase were analyzed for lipase content using the ANTEK model 707 Chemiluminescent Nitrogen Analyzer. For example, 8.0 g of HDPE Accurel ® powder were placed in a glass column, wet with 100 mls of 3A-ethanol, rinsed with 200 mls of buffered water, contacted with 100 mls of lipase solution containing 1.0 g of lipase dissolved in 100 mls of buffered water, and then rinsed with 150 mls of buffered water. Analysis of the lipase solution before and after contact with the support indicated that 64.5% of the lipase was removed from solution. Assuming all the removed lipase was immobilized on the powder, the support contained $(0.645 \text{ g}/(8.0+0.645)\text{g}) \times 100\% = 7.5\%$ lipase w/w.

The fixed bed reactors were glass columns jacketed with plexiglass sleeves. The columns were maintained at 40° C., by circulating water baths. The actual column dimensions varied. Continuing the example involving 8.0 g of HDPE powder, the dimensions of the fixed bed were 1.7 cm diameter by 21 cm in length (48 cm$^3$).

Substrate was pumped into the columns (5–20 ml/hr), with a piston pump to maintain close control over the rate. The substrate most used was 25/75 olive oil/0.1M, pH 7.0 phosphate buffer. Two column flow patterns were investigated: (1) countercurrent flow of the buffered water (enters column at top) and olive oil (enters at bottom), and (2) cocurrent flow of the oil and buffered water (both enter at bottom).

FIG. 1 illustrates the cocurrent fixed bed immobilized lipase reactor. Triglycerides (TG) and buffered water were pumped in the bottom of the column. As mentioned earlier, a variety of Accurel ® materials were tried as support for the lipase. Table 4 below compares the % FA obtained from three fixed bed cocurrent reactors operated under conditions which were similar except for support material:

TABLE 4

| Support | Weight (gm) | % FA |
|---|---|---|
| PP, melt blown fibers | 4 | 34 |
| HDPE granules | 10 | 42 |
| HDPE powder | 8 | 94 |

Since the HDPE powder, 150–450 micron particle size, was clearly a superior support to a very surprising and unexpected extent as compared to the fibers, this powder was used in all the subsequent reactor columns. Conditions for two of these columns are given below:

| | Column I | Column II |
|---|---|---|
| Substrate: | 25/75 o.oil/buffered water | 25/75 o.oil/buffered water |
| | Emulsion Feed | Separate Feed |
| Total Flowrate: | 10–15 ml/hr | 20 ml/hr |
| Temperature: | 40° C. | 40° C. |
| Support wt: | 8.0 gm | 10.0 gm |
| Bed size: | 1.7 cm diameter × | 2.1 cm diameter × |

-continued

| | Column I | Column II |
|---|---|---|
| | 21 cm length | 18 cm length |
| Lipase adsorbed: | 650 mg. | 975 mg. |

Figure 6:
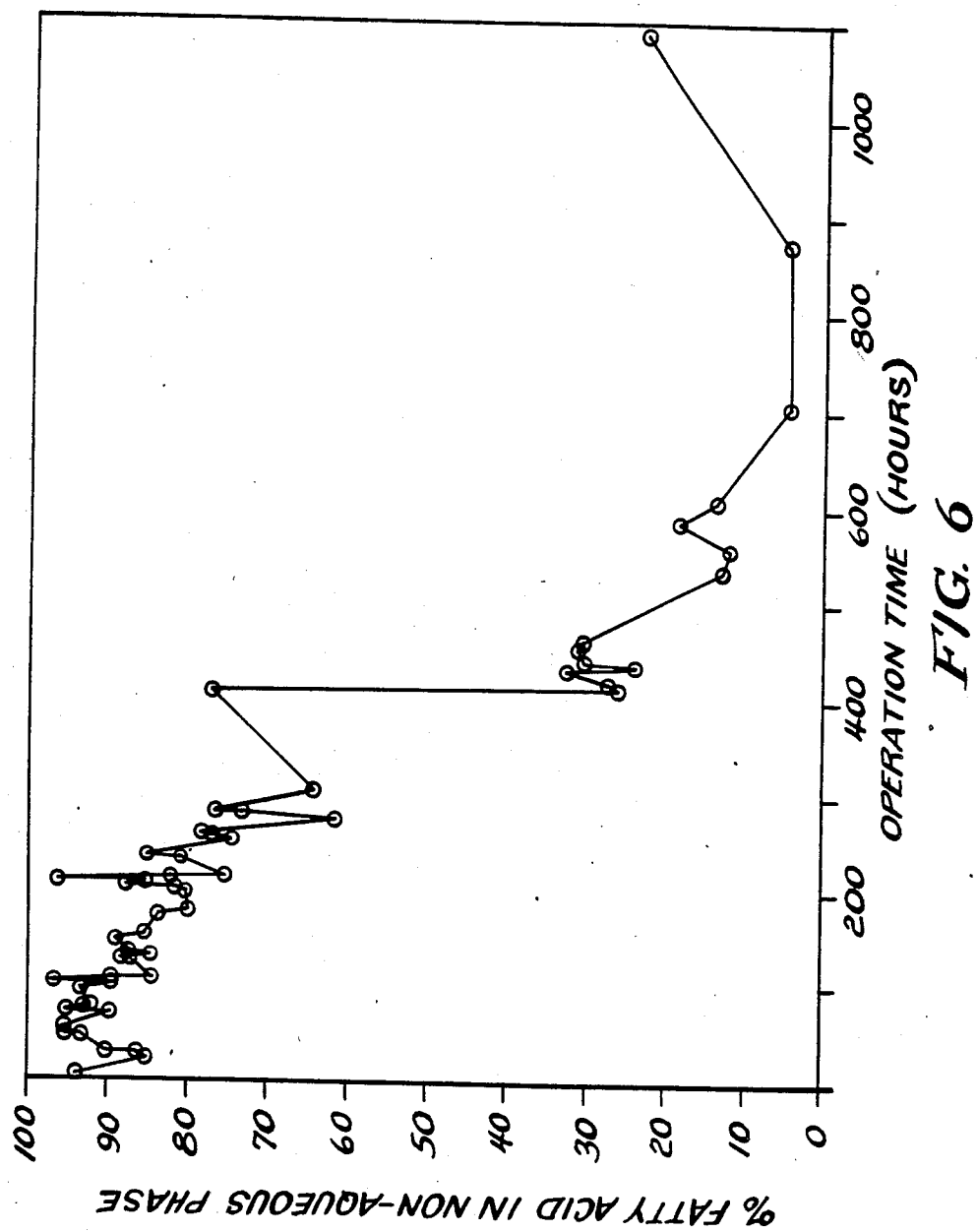
FIGS. 6 through 11 comprise graphic presentations of data obtained as described in the examples.

Column I was still in operation after 1100 hours. In this column the olive oil and buffered water were mixed together in a beaker prior to entering the column. Continuous agitation was supplied to the emulsion by a magnetic stirrer. A single pump drew off emulsion to feed the column. The volumes of buffer and oil that flowed out of the column were recorded daily. Considerable variation was observed in the ratios of oil:water that were collected from the 25:75 ratio which was supplied to the emulsion reservoir. Thus, throughout the run of this column, the substrate composition was not fixed. The half-life (time for the activity of the immobilized lipase to decrease by 50%) of the immobilized lipase in this column was 234 hrs. The results for this column in terms of % fatty acid in the nonaqueous product over time are graphically shown in FIG. 6.

Figure 7:
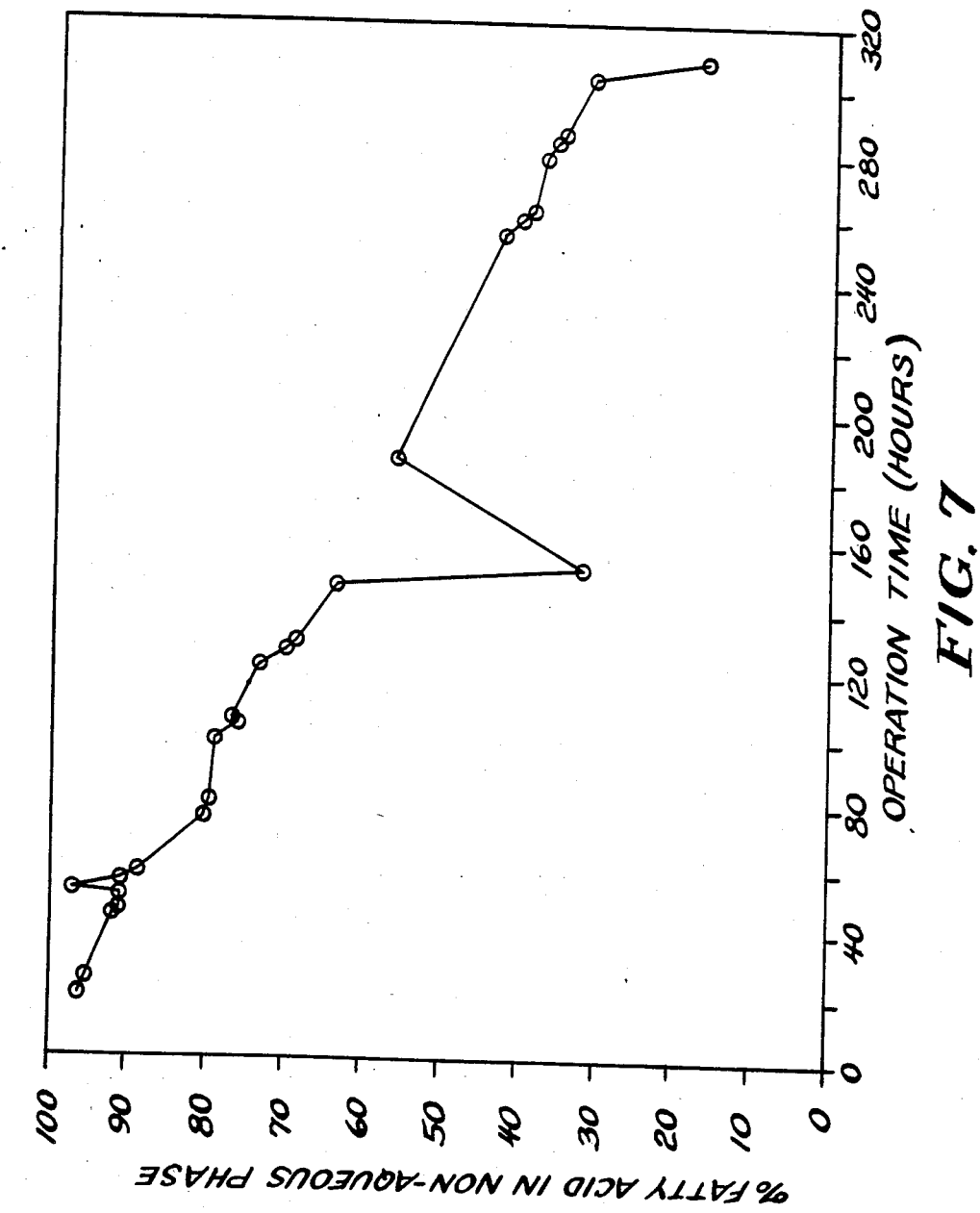

Column II was operated for 310 hours before being terminated. This column had a higher support load and a higher support:lipase ratio in hopes of increasing the half-life of the lipase. In addition, separate pumps were used to pump the olive oil at 5 ml/hr and the buffered water at 15 ml/hr in order to maintain a constant substrate composition to the column. Also, in the bottom of the column was a glass frit which was used to break the oil into smaller droplets before contact with the lipase. This column in spite of the efforts made, achieved a half-life of only 157 hrs. The results for this column are graphically shown in FIG. 7.

FIG. 2 illustrates the countercurrent fixed bed immobilized lipase reactor. The column bed contained 10 grams of HDPE Accurel ® granules. Lipase was immobilized on the granules prior to packing of the column. The catalyst bed measured 2.5 cm diameter by 26 cm in length.

Buffered water was pumped into the top of the column and out the bottom at 5 ml/hr by using two pump heads on the same pump drive. Olive oil was pumped in the bottom of the column at approximately 10 ml/hr. Problems were encountered in balancing the flows of the oil and water to maintain a steady state in the column. Yields of only 10–20% FA were obtained on the olive oil substrate, but it is believed that far better results will be obtained from this embodiment of the invention once it is optimized.

EXAMPLE 6

Figure 8:
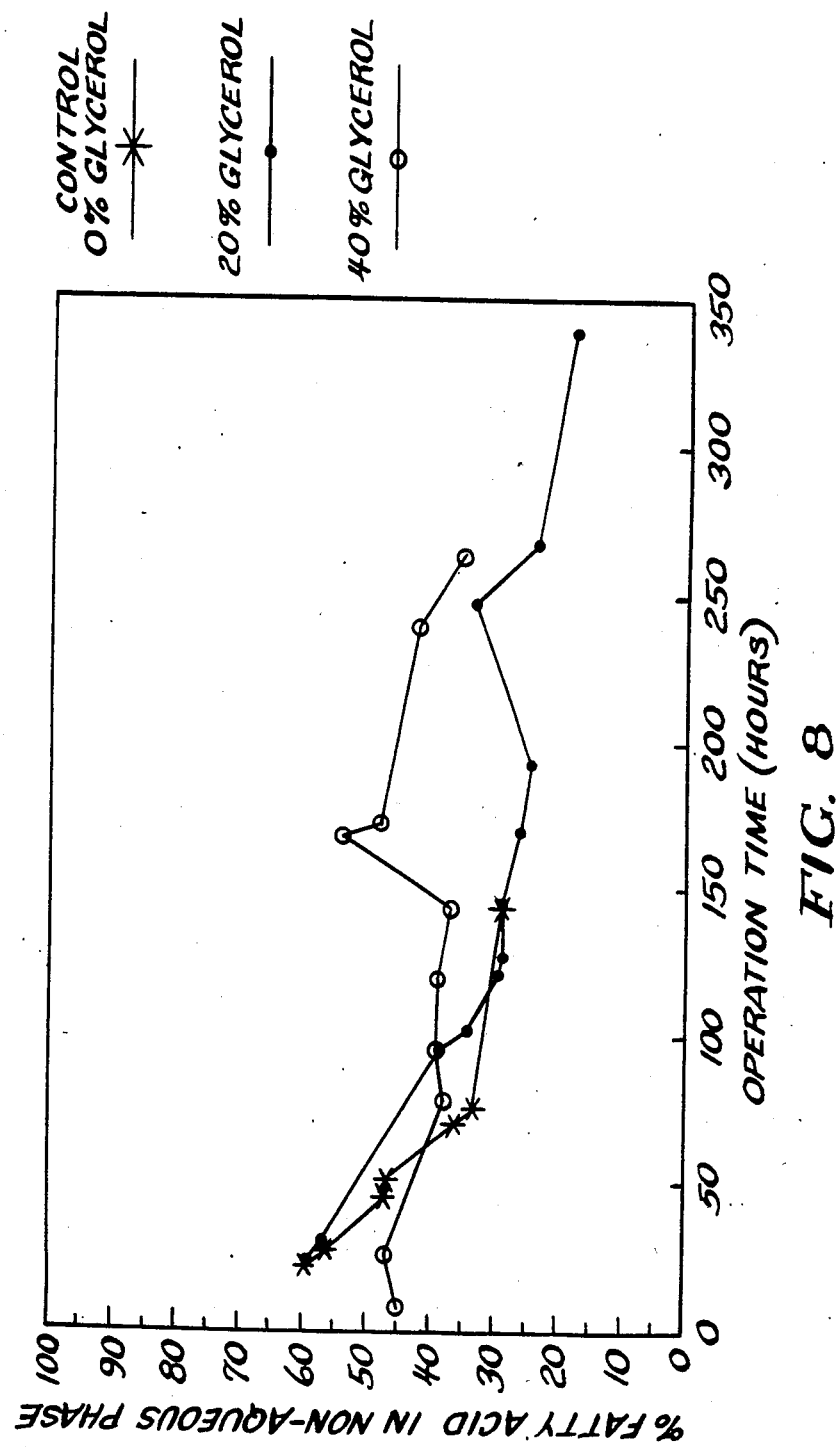

A study was made using the fixed bed co-current flow column reactor of the effect of maintaining a high glycerol content in the water phase. It was observed that such content had a profound effect in maintaining the activity of the lipase although there is a reduction in the degree of fat splitting due to reaction equilibrium effects. FIG. 8 comprises a plot of data of the fat split obtained over an extended period of time with the reaction medium having various levels of glycerine concentration, and shows the surprising improvement in lipase longevity that can be achieved by maintaining a concentration of about 40 wt.% glycerol. Concentrations in excess of 40 wt.% would probably not be practical because of the low conversion of fats that would be obtained.

EXAMPLE 7

The vertical diaphragm reactor embodiment of the invention is shown in FIG. 3. The reactor was constructed of 6" plexiglass pipe, contained a lower olive oil reservoir and an upper buffered water reservoir. Olive oil was pumped into the lower reservoir and was forced up through the diaphragm that separated the upper and lower reservoirs. The diaphragm was supported on top and bottom by plastic mesh screens. The diaphragm itself consisted of three layers including the top screen. Olive oil first passed through the bottom layer which was a teflon filter cloth which broke the oil into fine droplets. Next the oil passed up through a middle layer comprising a pad of lipase immobilized on melt blown polypropylene Accurel ® fibers made by Enka America Incorporated. The fat was split as it passed through the pad. The fatty acid then rose to the top of the upper reservoir which was initially filled with 1.8 L of 0.05M EDTA buffered water at pH 7.0, to form an uppermost phase. Overhead agitation was supplied to the upper reservoir.

To evaluate the operational stability of the immobilized lipase, this diaphragm reactor was run in a batch mode for approximately two months. The reactor contained 5.0 g of melt blown Accurel ® polypropylene fibers that contained approximately 0.3 g. of lipase from Candida (Enzeco ® as stated above). Each day, 450 mls of olive oil were fed into the reactor by gravity feed over a 6 hour period. At the end of 6 hours, the fatty acid layer on top of the upper reservoir was analyzed by GPC. The top reservoir was then emptied and filled with fresh buffer the following day.

Figure 9:
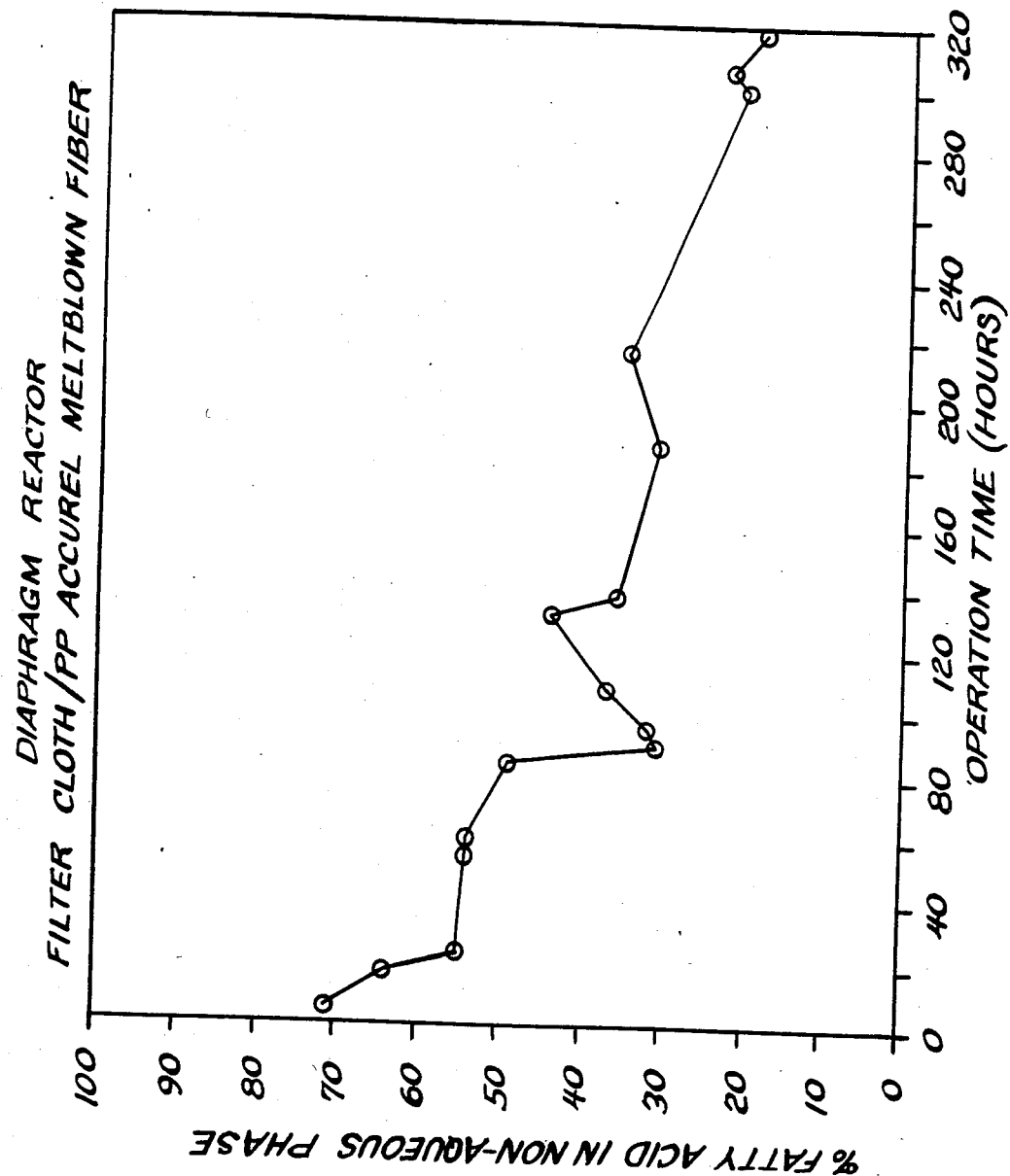

The plot of % FA versus time in hours, as shown in FIG. 9, gives an indication of the half-life of the immobilized lipase. Linear regression of % FA versus time of actual operation indicates a half-life of 223 hours.

One can use data from the first day to calculate an estimate of the productivity of the reactor. On that day 450 mls of 71% FA were collected to arrive at a production rate of 301 mg FA/hr/cm$^2$.

EXAMPLE 8

This example illustrates the stirred reactor embodiment of the present invention as shown in FIG. 5.

In a first test run immobilized *Candida cylindracea* lipase (Maxazyme LP from Gist-Brocades N.V.) was prepared in the following manner:
1. 10.0 gm of HDPE Accurel ® powder (150–450 μm diameter) was wetted with 20.0 ml of 3A ethanol.
2. 1.0 gm of Maxazyme LP lipase was dissolved in 100 ml of 0.1M Na$_2$HPO$_4$ in aqueous solution at pH 7 by stirring for 10 min.
3. The lipase solution was centrifuged to remove any unsoluble material.
4. The lipase solution was added to the wetted Accurel ® powder and stirred for 30 min.
5. The immobilized Accurel ® powder was filtered using a Buchner funnel and washed with 300 ml of buffered water before it went into the reactor.

A bench scale reactor was constructed comprising a 500 ml round bottom flask with four necks. Two of the necks were for the inlet of liquid fats (oil) and buffered water, the third was for the product stream outlet, and the fourth was for an overhead stirrer. A glass wool plug was placed in the product stream outlet neck.

The 500 ml flask was filled with deionized water. Then the above immobilized enzyme was added. The reactor was assembled, an overhead stirrer started, and two feed pumps were turned on, one for each of the feed streams with a combined flow rate of 12 ml/hr. and a volume ratio of oil to water of 4.5/7.5. The reaction was at room temperature.

Figure 10:
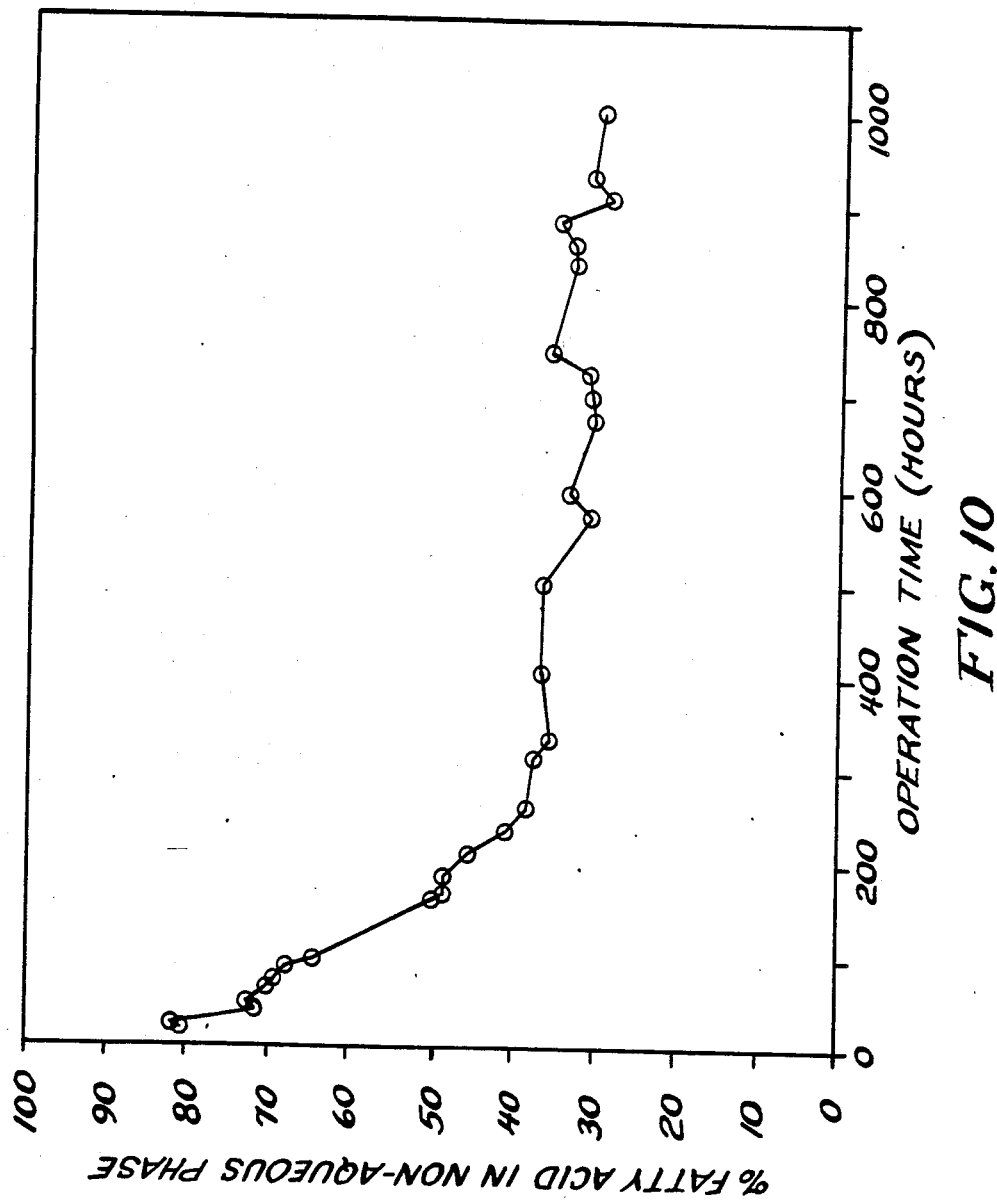

The results of the first test run are shown in FIG. 10 in terms of fatty acid concentration in the non-aqueous product phase vs. time. The figure shows a rapid initial fall-off in conversion of fats to a rather low constant level.

The first test run was repeated except that 2.0 g. of lipase immobilized on 20.0 g. of support were added to the reactor. All other conditions and details of the procedure and apparatus remained the same. The results are shown in FIG. 11.

Figure 11:
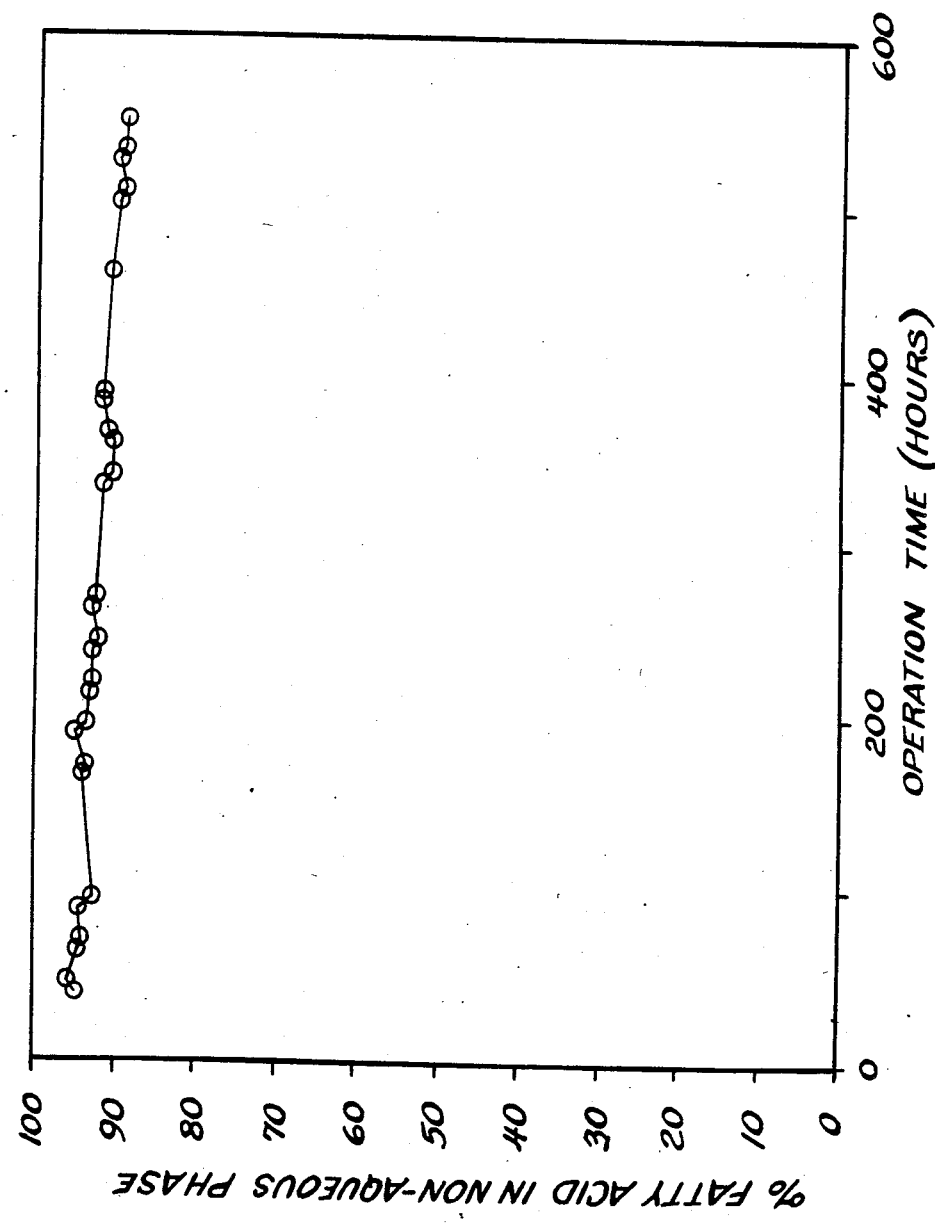

The results of FIG. 11 are startling. Unlike in the first test run where less amount of lipase was present, in the second run there was no initial fall-off of conversion and almost no fall-off of conversion even after 600 hours of operation were approached. There thus appears to be an amazing and unexpected criticality in a minimum amount of lipase that must be present in the reactor mixture for optimum effect.

Since it was determined that only about 65% of lipase initially introduced into the CSTR reactor is retained on the support within a short time after initiation of the test runs, the critical lipase concentration is calculated to be about 2.5 g per liter of reactor volume for the oil charge rate of 4.5 ml/hr, or 556 grams per liter of reactor volume per liters per hour of liquid fat charge.

EXAMPLE 9

This example provides a further comparison of the performance of the previously discussed embodiments of the present invention comprising the diaphragm, cocurrent fixed bed and stirred tank reactors. In each case the embodiment used was the one known to be the optimum, including the diaphragm as described in Example 7, the cocurrent fixed bed as in Example 5 with the HDPE Accurel ® Powder and the stirred tank and immobilized lipase on Accurel ® was described in Example 8

The results of the comparison are shown in Table 5 where the half-life (in hours) and productivity (pounds fatty acid produced per pound of immobilized lipase) are given for each embodiment. Two runs were made for each of the fixed bed and stirred reactor embodiments.

The results show that the diaphragm clearly comprises the best mode of the process of the invention at least as far as productivity is concerned. In the course of the half-life of the immobilized lipase in the diaphragm, the productivity of the diaphragm was over five times that of the best run of the stirred reactor and over ten times that of the fixed bed reactor.

It was also observed that the production rate of the diaphragm in terms of mg/hr. per cm$^2$ of fatty acid produced was, depending on the choice of hydrophobic filter cloth, as high as 301.

TABLE 5

IMMOBILIZED LIPASE REACTOR SUMMARY
Olive Oil Substrate

| Type | Half-Life (hours) | Productivity $\frac{\text{lbs FA}}{\text{lbs IME}}$ |
|---|---|---|
| Diaphragm | 223 | 1695 |
| Fixed Bed | 378 | 119 |
| (Powder columns) | 207 | 88 |
| Stirred Reactor | 348 | 342 |
|  | 468 | 274 |

As can be seen from the above examples, and corresponding FIGS. 6 through 11, regardless of the embodiment of the invention employed, whether it be a packed column reactor with cocurrent or countercurrent flow, a diaphragm reactor or a stirred reactor, not only is the initial activity of the immobilized lipase comparable to that of free lipase, the activity remains usefully high for a significant time. Enzymatic fat splitting has thus become an economic reality.

What is claimed is:

1. A diaphragm suitable for use in the hydrolysis of fats comprising:
   a. a first layer comprising of a hydrophobic filter cloth having openings from about 3 to about 5 microns in size;
   b. a second layer adjacent to said first layer comprising fibers of a hydrophobic microporous thermoplastic polymer, having lipase immobilized on said fibers by adsorption from an aqueous solution either without pretreatment or following pretreatment of said fibers only by wetting with a polar water miscible organic solvent in which said polymer is insoluble and which does not deactivate said lipase; and
   c. a third layer adjacent to the side of said second layer opposite said first layer comprising a retaining means capable of maintaining said fibers of said second layer in place.

2. The diaphragm of claim 1 wherein said microporous structure is cellular and comprises a plurality of substantially spherical cells having an average diameter from about 0.5 to about 100 microns, distributed substantially uniformly throughout the structure, adjacent cells being interconnected by pores smaller in diameter than said microcells the ratio of the average cell diameter to the average pore diameter being from about 2:1 to about 200:1, said pores and said cells being void.

3. The diaphragm of claim 1 wherein said microporous structure is cellular and is characterized by a C/P ratio of from about 2 to about 200, an S value of from about 1 to about 30, and an average cell size from about 0.5 to about 100 microns.

4. The diaphragm of claim 1 wherein said microporous polymer structure is isotropic and is characterized by an average pore diameter of from about 0.1 to about 5 microns and an S value of from about 1 to about 10.

* * * * *